United States Patent

Neumann et al.

[11] Patent Number: 6,084,414
[45] Date of Patent: Jul. 4, 2000

[54] TESTING FOR LEAKAGE CURRENTS IN PLANAR LAMBDA PROBES

[75] Inventors: Harald Neumann, Vaihingen; Walter Strassner, Schorndorf; Lothar Diehl, Stuttgart, all of Germany

[73] Assignee: Robert Bosch GmbH, Stuttgart, Germany

[21] Appl. No.: 09/061,438

[22] Filed: Apr. 16, 1998

[30] Foreign Application Priority Data

Apr. 18, 1997 [DE] Germany ............... 197 16 173

[51] Int. Cl.[7] .................. G01R 31/02; G01N 27/416
[52] U.S. Cl. .................. 324/468; 324/523; 204/426; 73/23.2
[58] Field of Search ................. 324/500, 511, 324/522, 523, 537, 555, 556, 713, 718, 72.5, 464, 468; 204/410, 421, 425, 426, 427; 73/23.31, 23.32; 123/688; 700/300

[56] References Cited

U.S. PATENT DOCUMENTS

| | | | |
|---|---|---|---|
| 5,291,417 | 3/1994 | Schaibel et al. | 700/300 |
| 5,399,961 | 3/1995 | Wild et al. | 73/23.32 |
| 5,439,581 | 8/1995 | Schmah | 204/427 |
| 5,562,811 | 10/1996 | Lenfers | 204/426 |
| 5,875,768 | 3/1999 | Schenk et al. | 73/23.31 |

Primary Examiner—Diep N. Do
Attorney, Agent, or Firm—Kenyon & Kenyon

[57] ABSTRACT

A method for testing for leakage currents in an oxygen probe, in particular a planar lambda probe, having at least one heating element, one external electrode and one internal electrode, and a solid electrolyte arranged between the electrodes, a first voltage being applied to the heating element. A second voltage is applied to at least one of the electrodes, the second voltage being selected so that the potential difference between the electrode and at least one area of the heating element is positive.

6 Claims, 1 Drawing Sheet

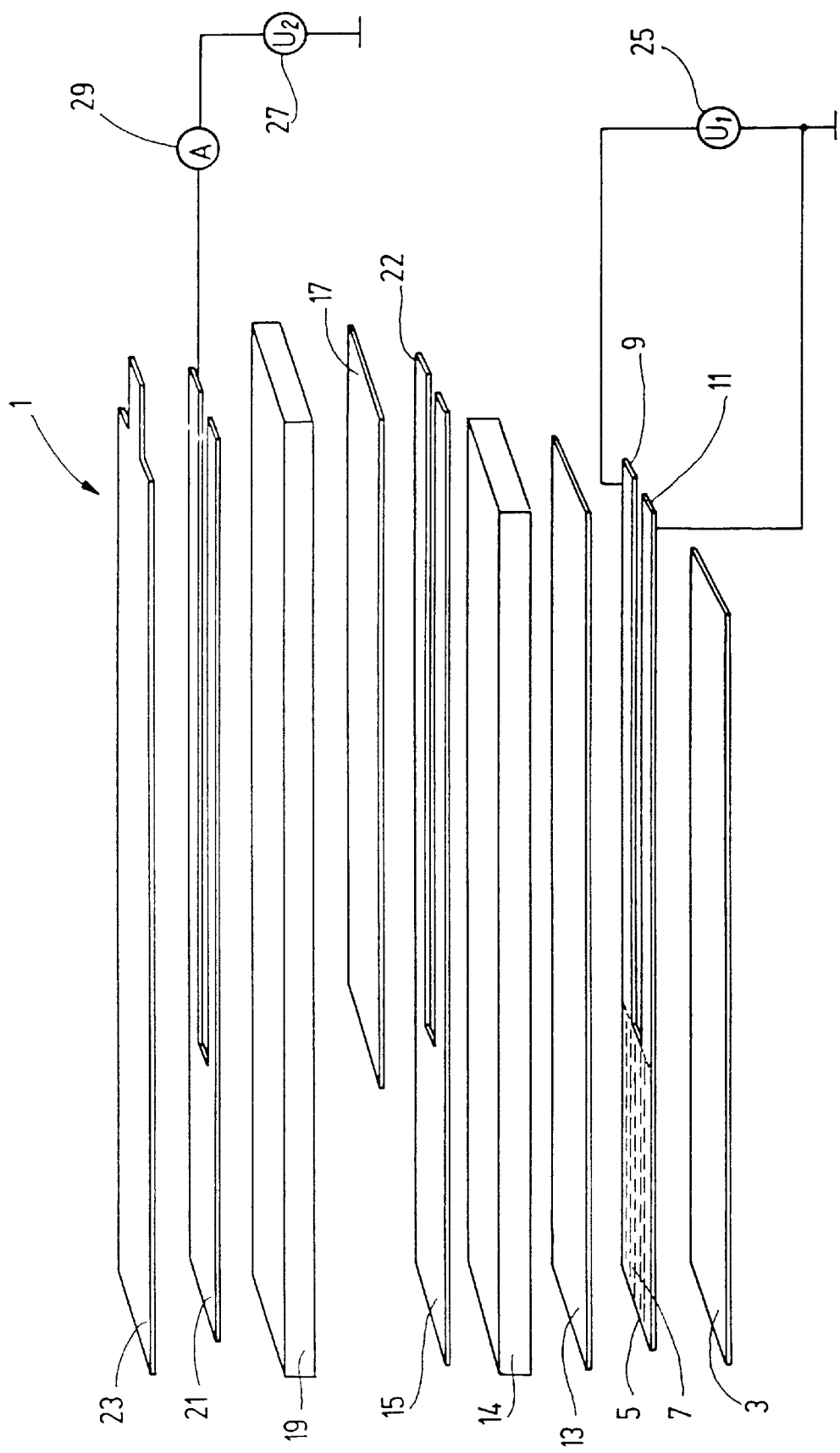

TESTING FOR LEAKAGE CURRENTS IN PLANAR LAMBDA PROBES

FIELD OF THE INVENTION

The present invention relates to a method for testing for leakage currents in an oxygen probe, in particular a planar lambda probe, having at least one heating element, one external and one internal electrode, and a solid electrolyte arranged between these two electrodes, the heating element receiving a first voltage.

BACKGROUND INFORMATION

Processes for testing for leakage currents in lambda probes are known. In general, lambda probes have two electrodes with a solid electrolyte between them. Furthermore, a heating element is provided, which is electrically insulated from both electrodes by means of an insulating layer. If this insulating layer has one or more electric leakage points, a leakage current is formed between the heating element and one of the electrodes; as oxygen concentration is measured, the current is superimposed on the measuring current in the lambda probe and distorts the measurement results.

To measure this leakage current, a voltage is usually applied to the heating element, and the current flowing through the electrode referred to as the external electrode is measured. For this purpose, the external electrode is connected to ground via an ammeter. If the insulation between the heating element and this external electrode has an electric leakage point, the ammeter will show a value after a voltage is applied to the heating element which, if it exceeds a limit value, indicates a leakage point. This leakage current, established after a transient process, forms the quasi-stationary leakage current hereinafter referred to as leakage current.

The disadvantage of this method is that $O^{2-}$ ions accumulate to form a space charge at the leakage point in the insulation layer. An electric field, which is of opposite polarity with respect to the field between the heating element and the external electrode, is formed between the space charge and the heating element, thereby reducing the ion stream flowing to the external electrode. Therefore smaller leakage points in the insulation cannot be detected.

Another disadvantage of this method consists of the fact that the external electrode and one terminal of the heating element are at a common potential. Therefore leakage points in the proximity of this terminal of the heating element cannot be detected due to the lack of difference in potential.

SUMMARY OF THE INVENTION

The method of the present invention has the advantage over the related art that the leakage current is considerably greater and the position of the leakage point can be located through a discoloration on the surface of the lambda probe. For this purpose, a second voltage that is greater than the voltage applied to the heating element is applied to the external electrode or the internal electrode. As a result, no space charge is formed on the insulation layer, but rather the $O^{2-}$ ions migrate, following the electric field, from the leakage point in the insulation to the external electrode or the internal electrode. The measurable leakage current is therefore not reduced by a space charge and has a considerable greater value. Compared to the known procedure, 10 to 100 times greater leakage currents are measured. Thus even smaller leakage points are advantageously detected.

Another advantage results from the fact that the positive voltage between the electrode and the heating element allows leakage points to be detected over the entire area of the insulation layer, in particular also in the area of the heating element's ground terminal, due to the potential difference that is always present.

Another advantage of the method according to the present invention is the fact that the $O^{2-}$ ions migrating to the external electrode cause a reduction reaction in the solid electrolyte, resulting in a black coloration extending to the surface of the lambda probe, thus indicating the position of the leakage point in the insulation. Thus, the method according to the present invention advantageously allows leakage points in any location in the insulation to be located and small leakage points to be detected due to the higher leakage currents.

BRIEF DESCRIPTION OF THE DRAWING

The FIGURE shows an exploded view of a lambda probe and the measurement setup according to the present invention.

DETAILED DESCRIPTION

The FIGURE schematically shows the layer structure of a lambda probe 1, which is relevant to the method according to the present invention. Lambda probe 1 has an approximately rectangular cover 3, for example, in the form of a foil, and a heating element 5 arranged in a layer above it, which can also be configured as a foil. Conducting paths 7 in a winding pattern form heating element 5 and are electrically connected to terminals 9 and 11 also configured as conducting paths. An insulating layer 13 and a solid electrolyte 14 are arranged over heating element 5. Insulating layer 13 has the function of insulating heating element 5 from a first electrode 15 arranged over insulating layer 13. In the other layers of lambda probe 1, this electrode 15 is followed by another solid electrolyte 19 and a second electrode 21, which is hereinafter referred to as the external electrode.

Conductors 22, electrically insulated from solid electrolyte 19 by an insulation layer 17, are connected to electrode 15, referred to as the internal electrode. The two electrodes 15 and 21 form, together with solid electrolyte 19, the part of lambda probe 1 which serves for measuring the oxygen concentration of a gas. External electrode 21 is covered by a cover 23, which serves as the upper boundary of lambda probe 1.

In the method according to the present invention for measuring a leakage current, a voltage $U_1$ of 15 V, for example, delivered by a d.c. current source, is applied to terminals 9, 11 of heating element 5, terminal 11 being connected to ground. The area to be tested of the solid electrolyte is heated with this voltage to an operating temperature of approximately 600° to 800° C. A second voltage $U_2$ is applied to the second electrode 21 from second d.c. source 27; voltage $U_2$ is greater than voltage $U_1$ with respect to ground, preferably by the decomposition voltage of the solid electrolyte, being equal to 30 V, for example. This results in a potential difference of <15 V between the external electrode and an arbitrary point of heating element 5, while the potential difference is approximately 30 V between the electrode and the heating element in the area of the ground terminal and approximately 15 V in the area of positive terminal 9. It is important for the method according to the present invention that the potential $U_2$ is selected so that the potential difference between the ground electrode (external or internal electrode) and an arbitrary point of heating element 5 is greater than the decomposition voltage of the solid electrode.

An ammeter 29, serving for measuring the leakage current, is also connected into the line between voltage source 27 and second electrode 21. In the event of a leakage point in insulation layer 13, the two voltages $U_1$ and $U_2$ and the positive potential difference between the external electrode and heating element 5 have the following effect:

Due to the aforementioned potential difference, an electric field is formed between external electrode 21 and heating element 5. Solid electrolyte 19, made of $ZrO_2$, has a high ion conductivity, so that $Zr^{4+}$ and $O^{2-}$ ions are formed in the electric field. The leakage point in insulation layer 13 results in an electric connection between solid electrolyte 19 and heating element 5, and generates a current of charged particles flowing to heating element 5. In the same manner, the $O^{2-}$ ions migrate to the external electrode under the effect of the electric field, are converted into atomic oxygen by releasing two electrons, and diffuse through the gas-permeable cover 23 as oxygen to the outside. The electrons released are then discharged via voltage source 27, this current being detectable as a leakage current by ammeter 29. A high concentration of oxygen holes is formed in solid electrolyte 19 due to the release of oxygen; the holes are visible as a black coloration extending to the surface of lambda probe 1. Since this path formed in lambda probe 1 is basically a straight line, the position of the external visible black coloration indicates the position of the leakage point.

What is claimed is:

1. A method for testing for a leakage current in an oxygen probe, the oxygen probe including at least one heating element, an external electrode, an internal electrode, and a solid electrolyte arranged between the external and internal electrodes, the method comprising the steps of:

applying a first voltage to the at least one heating element;

applying a second voltage to at least one of the external and internal electrodes to establish a positive potential difference between, on the one hand, the at least one of the external and internal electrodes and, on the other hand, at least one area of the at least one heating element; and testing for the leakage current as a consequence of the positive potential difference.

2. The method according to claim 1, wherein the oxygen probe is a planar lambda probe.

3. The method according to claim 1, wherein the second voltage is greater than the first voltage.

4. The method according to claim 1, wherein the second voltage is greater than a sum of the first voltage and a decomposition voltage of the solid electrolyte.

5. The method according to claim 1, further comprising the step of heating the solid electrolyte to a temperature between 600° and 800° C. in an area to be tested.

6. The method according to claim 5, wherein an external heating device is used to heat the solid electrolyte, wherein the first voltage is equal to zero, and wherein the second voltage is at least as great as a decomposition voltage of the solid electrolyte.

* * * * *